United States Patent
Sachdeva et al.

[11] Patent Number: 5,791,899
[45] Date of Patent: Aug. 11, 1998

[54] BONE ANCHORING APPARATUS AND METHOD

[75] Inventors: Rohit Chaman Lal Sachdeva, Plano, Tex.; Petrus Antonius Besselink, Enschede, Netherlands

[73] Assignee: Memory Medical Systems, Inc., Plano, Tex.

[21] Appl. No.: 660,519

[22] Filed: Jun. 7, 1996

Related U.S. Application Data

[63] Continuation of Ser. No. 207,441, Mar. 7, 1994, Pat. No. 5,584,695.

[51] Int. Cl.⁶ .................................................. A61C 8/00
[52] U.S. Cl. .................................................. 433/173; 623/16
[58] Field of Search ........................ 433/172, 173, 433/174, 175, 176, 177; 606/60, 61, 69, 70, 71, 72, 73, 74, 75, 76, 77, 78; 623/11, 13, 16, 17

[56] References Cited

U.S. PATENT DOCUMENTS

| | | |
|---|---|---|
| 4,468,201 | 8/1984 | Fukuyo .................. 433/176 |
| 5,061,285 | 10/1991 | Koch . |
| 5,108,289 | 4/1992 | Fukuyo .................. 433/173 |
| 5,174,755 | 12/1992 | Fukuda .................. 433/173 |
| 5,190,546 | 3/1993 | Jervis .................... 606/78 |
| 5,219,287 | 6/1993 | Nishihara ............... 433/201.1 |
| 5,356,431 | 10/1994 | Pierce ................... 623/11 |

FOREIGN PATENT DOCUMENTS

| | | |
|---|---|---|
| 0180247 | 11/1985 | European Pat. Off. . |
| 3535266 | 5/1986 | Germany . |
| 92/02191 | 2/1992 | WIPO . |

*Primary Examiner*—Nicholas D. Lucchesi
*Attorney, Agent, or Firm*—Wood, Herron & Evans, L.L.P.

[57] ABSTRACT

A bone anchoring assembly and method for attaching a body part to a patient's bone which includes a bone anchor that is implantable in bone having an opening leading to a cavity formed therein. A coupling member with at least one portion made of a shape memory material having a transformation temperature range is disclosed. The coupling member is movable through the opening and in and out of the cavity at temperatures below the transformation temperature range. With it in the cavity and at temperatures above the transformation temperature range, the coupling member is locked within the bone anchor. The coupling member is attachable to the body part.

15 Claims, 4 Drawing Sheets

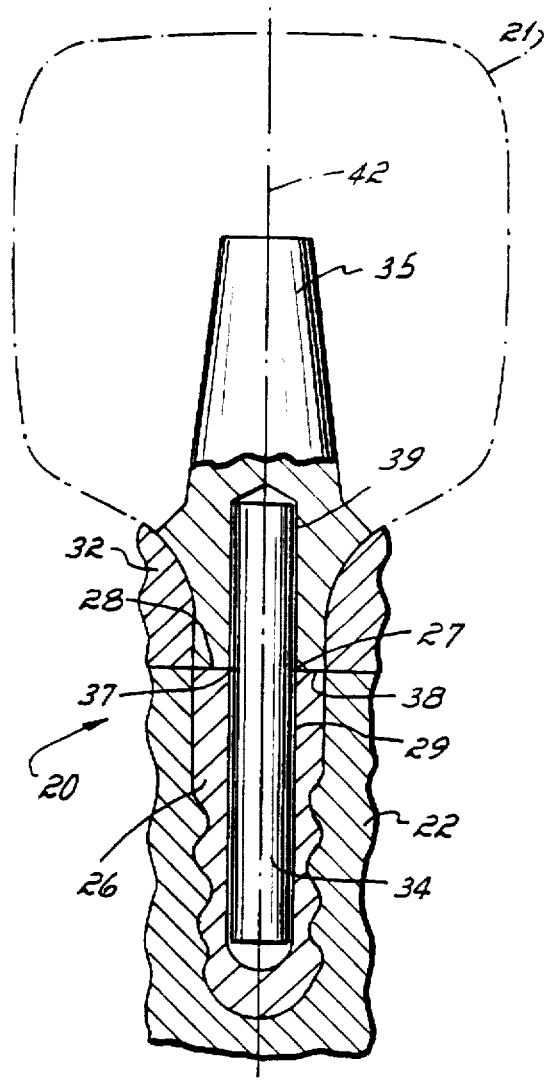
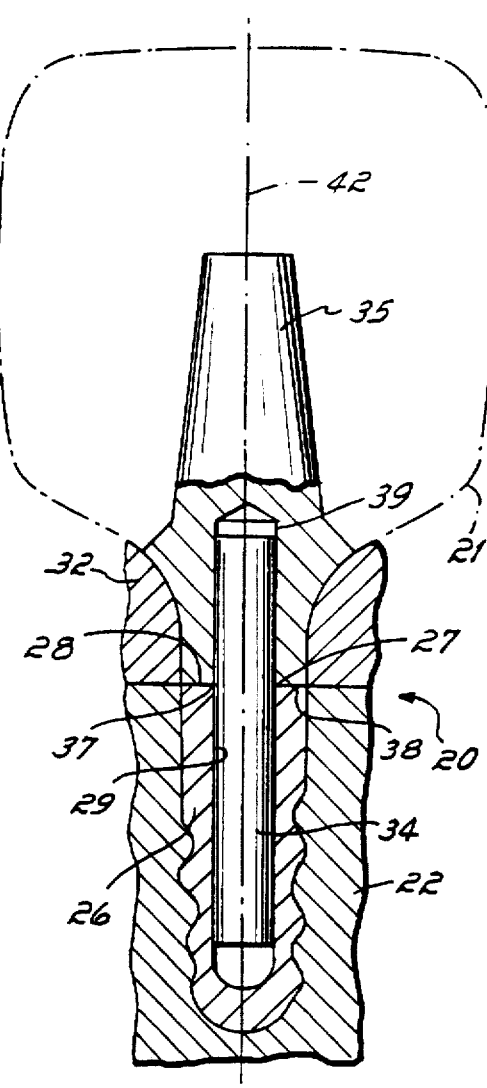
FIG. 1          FIG. 2
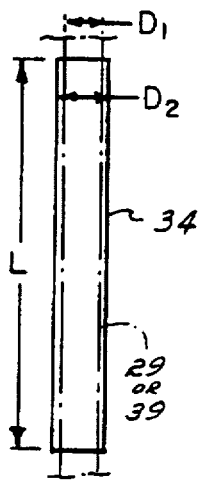
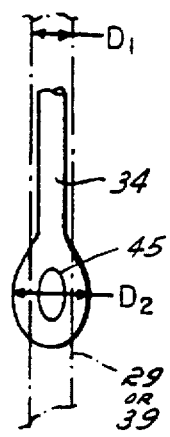
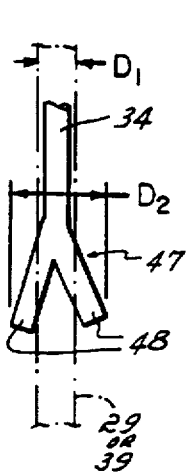
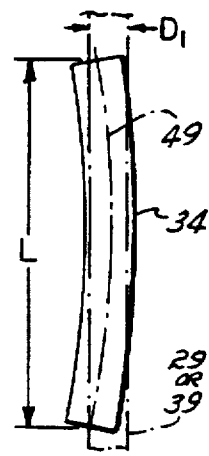
FIG. 2A    FIG. 2B    FIG. 2C    FIG. 2D

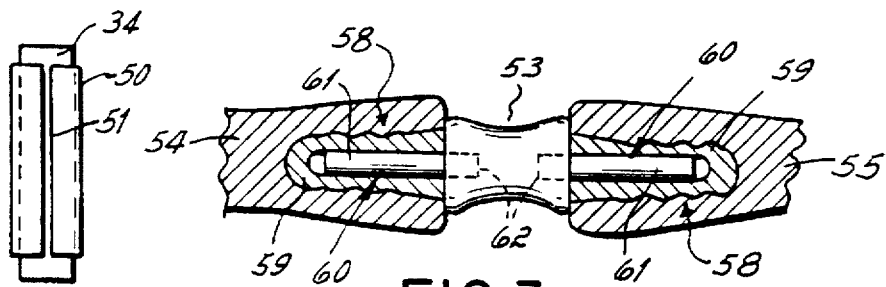
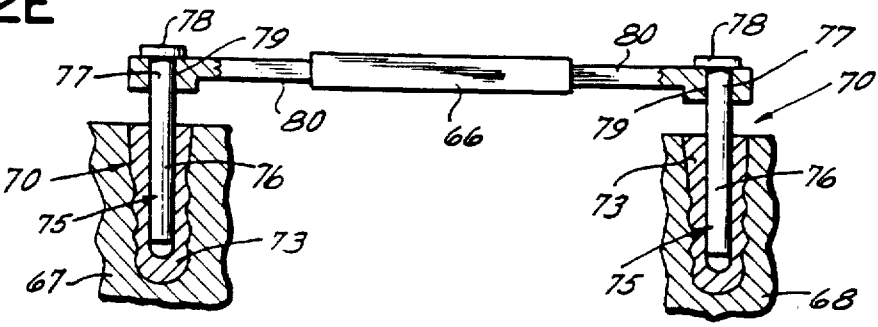
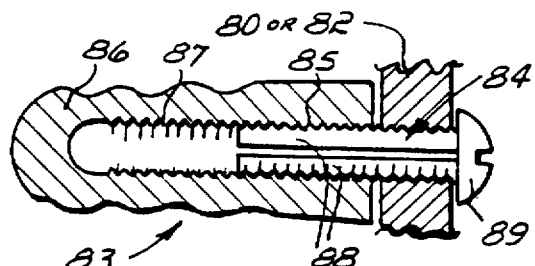
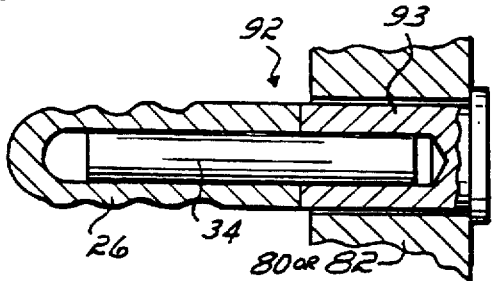
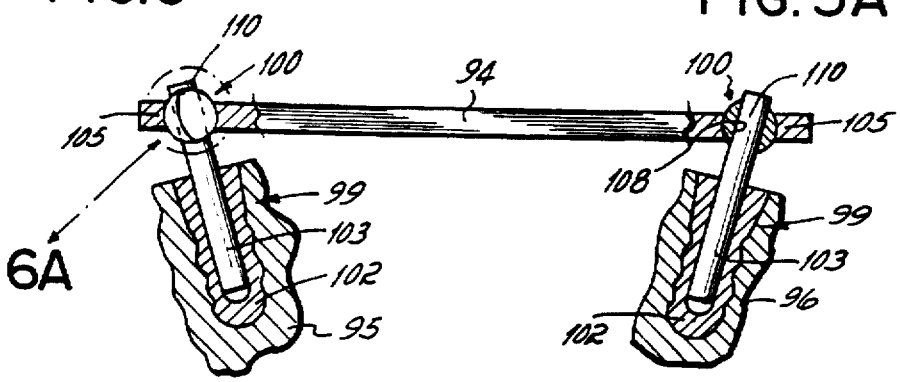
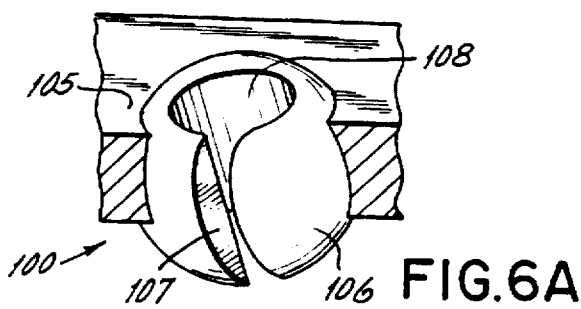

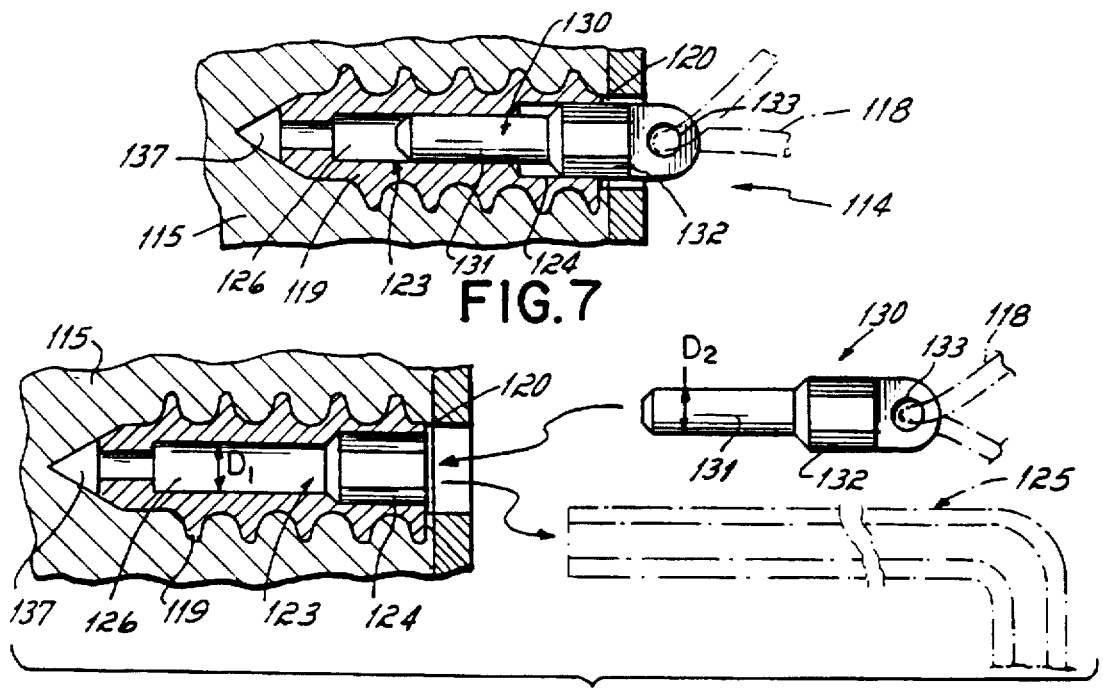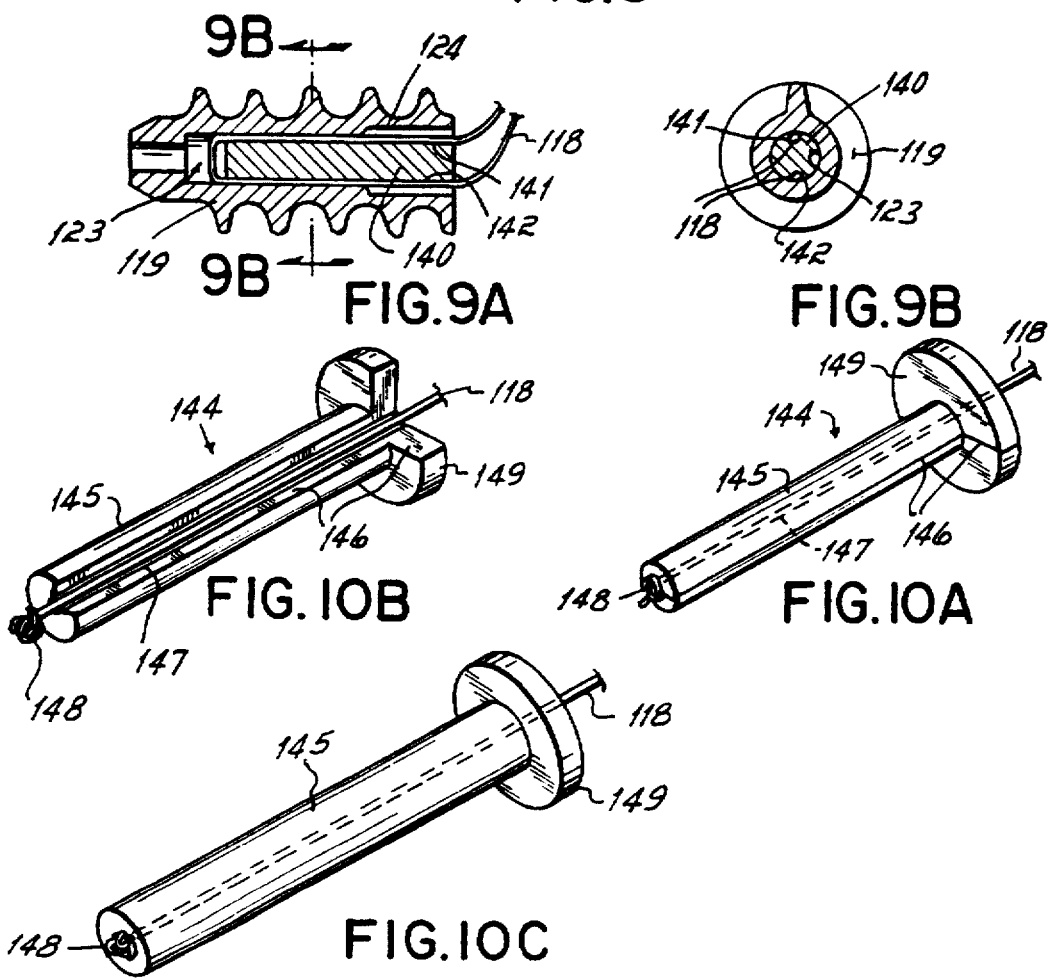

BONE ANCHORING APPARATUS AND METHOD

This is a continuation of application Ser. No. 08/207,441, filed Mar. 7, 1994, now U.S. Pat. No. 5,584,695

FIELD OF THE INVENTION

The present invention is related to a bone anchoring system, and more particularly to an apparatus and method for anchoring a body part to bone.

BACKGROUND OF THE INVENTION

In a number of medical procedures, one part of a patient's body is anchored to a desired location on one of the patient's bones. The body part being anchored may be living tissue, such as a ligament or bone, or a prosthetic replacement of an original body part. In one such procedure, a dental prosthesis, such as a crown or bridge, is used to replace one or more of a patient's teeth. Such dental prostheses have been anchored to bone using an anchoring assembly which included a bone anchor, such as a female bone screw or other endosseous implant, for being embedded in the patient's jaw bone. One such bone anchor has an opening leading to a threaded bore and a coupling member adapted at one end for being threaded into the bone screw bore. In another anchoring assembly, the coupling member is cemented into the bore formed in the bone anchor. The other end of the coupling member is fixed to the dental prosthesis. Sometimes the crown fractures off of the tooth leaving its root intact and embedded in the patient's jaw bone. In such situations, the tooth root may be used as the bone anchor, with the coupling member cemented or otherwise fixed within the tooth's root canal. One problem with such anchoring assemblies is that if the coupling member has to be removed, such as to replace the dental prosthesis, a force must be applied to the coupling member which is transmitted to the bone anchor. For example, if the coupling member is threaded into the bone anchor, a sufficiently high torquing force must be applied in order to unscrew and remove the coupling member. If the coupling member is cemented to the bone anchor, a sufficiently high force must be applied to break the cement bond between the coupling member and bone anchor.

Such female bone screws, or other bone anchors used with a coupling member, are preferably first implanted and left in the patient's bone for a period of time before the coupling member is secured to the bone anchor and an external force is applied to the bone anchor. This is done to permit the bone time to grow and bond with the bone anchor, thereby increasing the strength of the anchorage to the bone. The bone is less likely to bond to the bone anchor if an external force is applied soon after the bone anchor is implanted. Even if this bond is allowed to strengthen, the force required to remove the coupling member may be so high as to cause any bond between the bone anchor and the bone to weaken or even fail. In addition, screwing the threaded coupling member into the bone anchor may also apply a force of sufficient magnitude to weaken or even break the bond between the bone anchor and the bone. If this bond weakens or fails, the coupling member will likely need to be removed from the bone anchor in order to limit any external force applied to the bone anchor. Limiting such external forces is necessary in order to increase the likelihood that the bone-to-anchor bond will increase in strength. This additional delay in anchoring the body part to bone may inconvenience and cause additional discomfort to the patient.

Other problems associated with such anchoring assemblies may include the risk of the bone fracturing during removal of the coupling member from the bone anchor. This may also occur during insertion, particularly when a threaded coupling member is used. When the bone anchor is implanted, a comparable volume of bone is removed essentially leaving a cavity which may act as a stress concentrator. For smaller bones, such as some jaw bones, the amount of bone removed may significantly weaken the remaining bone at the anchoring site, making the bone more susceptible to fracturing when insertion or extraction forces are applied to the coupling member. In addition, when threaded coupling members are used, there is the risk that the threads will bind up. If this occurs, greater forces may need to be applied in order to insert and extract the coupling member. These greater forces may in turn cause the coupling member to fracture, typically at the threads. In order to subject the patient to as little discomfort as possible, it is typically desirable to complete the replacement procedure as quickly as possible. However, if there are spatial constraints, such as those associated with the small confines of a patient's mouth, attaching and removing the coupling member to and from the bone anchor may take more time than is desirable.

Other bone anchoring systems have been used to attach soft body tissue to a patient's bone. For example, certain orthopaedic surgical procedures require that a ligament be reattached to bone. Such ligament reattachment may occur, for example, in the knee or elbow where spatial constraints are typical. Such soft tissue attachment has typically been accomplished in the past by directly securing the soft tissue to the bone with a suture. Various types of bone anchors, such as bone screws, have been used in the past to anchor the suture to bone. These anchors are generally made of biocompatible stainless steel or similar non-corrosive metal such as titanium or chromium-cobalt alloys. Suture thread is attached to the anchor and the anchor is implanted directly into the bone.

When a patient's soft tissue, such as a torn ligament, must be reattached to bone, the torn end must be anchored to the bone and placed in close proximity to allow the ligament to grow into the bone mass and reattach itself. The closer the suture is anchored to the original point of attachment of the ligament, the better for body mechanics. Design limitations of prior art devices have been known to limit the optimal placement of the suture anchor and have lead to less efficient attachment of ligaments. Manipulation required to set the anchor into bone may impact upon the ability of the anchor to be used in locations having spatial constraints. The degree of manipulation required may prevent the use of less invasive surgical techniques, like arthroscopic surgery, and require the use of a more invasive technique to ensure that the anchor can be implanted at the optimal location. Some prior art anchors may just be unsuited for use in areas having spatial constraints. If a bone anchor is unsuitable for placement in the original location of ligament attachment, a nearby location having suitable space must be utilized. Another problem with such an anchoring device is that if the soft tissue ever detaches from the bone anchor or if the suture breaks, the screw may have to be removed and implanted again. Such reimplantation causes additional trauma to the bone which may ultimately result in the original bone anchoring site being unsuitable for subsequent anchoring.

Various anchoring systems have also been used to attach bone-to-bone, such as through the use of a bone plate, like that used in distraction osteogenesis devices or bone fixation plates. Typically, such devices are anchored to bone using screws or some other anchor implanted in the bone. These prior bone anchors typically must be removed from the bone if the device they are anchoring is to be removed or replaced. Again, the trauma to the bone caused by such reimplantation may result in the original bone anchoring sites becoming unsuitable for subsequent anchoring.

Therefore, there is a need for an anchoring system which enables a body part to be fixed to and detached from a patient's bone while eliminating, or at least substantially limiting, any additional trauma to the bone. More particularly, there is also a need for an anchoring system which if the body part is detached and reattached to the bone, the bond between the implanted anchor and the bone will not be substantially affected. There is also a need for such a bone anchoring system which may be anchored at locations on the bone that have spatial constraints using surgical procedures that are less intrusive and traumatic to the patient's body.

SUMMARY OF THE INVENTION

The present invention is directed to a bone anchoring assembly and method for attaching a body part to a patient's bone that enables the body part, whether prosthetic or the patient's, to be quickly attached to and removed from a particular location on the bone, even locations with spatial constraints. The present bone anchoring assembly and method also make it easier for the body part to be attached to and removed from spatially constrained locations on the bone with less intrusive surgical procedures and thus less trauma to the patient. Furthermore, the present bone anchoring assembly and method enable the body part to be attached to and removed from the same location on the bone with no substantial trauma to the bone in that location.

The anchoring assembly of the present invention includes a bone anchor that is implantable in bone. The bone anchor has an opening leading to a cavity formed therein. A coupling member, such as a pin, with at least one portion made of a shape memory material having a transformation temperature range (TTR) is used to couple the body part to the bone anchor. The one portion of the coupling member is movable through the opening and in and out of the cavity of the bone anchor when it is at a temperature below its TTR. With it in the cavity and at a temperature above its TTR, the one portion of the coupling member interlocks with the bone anchor. Preferably, the coupling member is insertable into and extractable from the cavity of the bone anchor with substantially zero insertion and extraction forces, respectively, when the one portion of the coupling member is at a temperature below its TTR.

Shape memory materials are generally relatively weak and pliable at least when the material is at a temperature below its TTR and relatively strong with superelastic properties at least when the material is at a temperature above its TTR. The properties of a given shape memory material typically vary within its TTR. Generally, the strength and superelastic characteristics tend to increase toward the high temperature end of its TTR and decrease toward the low temperature end. The characteristics of shape memory materials are well documented. For example, see the following published works: a book entitled *Engineering Aspects of Shape Memory Alloys*, 1990, published by Butterworth & Heinemann and edited by T. W. Duerig, K. N. Melton, D. Stockel and C. M. Wayman (ISBM No. 0-750-61009-3), including articles therein entitled "An Introduction to Martensite and Shape Memory" by C. M. Wayman and T. W. Duerig, pages 3–20; and "The Mechanical Aspects of Constrained Recovery", by J. L. Proft and T. W. Duerig, pages 115–129, each of which are incorporated by reference herein in their entirety. The unique properties of shape memory materials enable any structure made of such a material to have one geometric configuration at a temperature below its TTR and another geometric configuration at a temperature above its TTR. For purposes of the present invention, the working or ambient temperature of the anchoring assembly is typically a range of temperatures, preferably those temperatures normally found in the human body. The TTR of any shape memory portion of the present coupling member may fall below or overlap the working temperature(s) of the anchoring assembly.

Thus, the shape memory portion of the coupling member that interlocks with the bone anchor may be processed or trained, according to well-known techniques, to have a shape which can be easily inserted into or removed from the cavity of the bone anchor with little, if any, applied force when the shape memory portion is at least at a temperature below its TTR. Likewise, in order to lock the one shape memory portion of the coupling member and the bone anchor together, thereby anchoring the body part to the bone, the shape memory portion may be processed to have a shape which would not be removable from the bone anchor cavity at least at temperatures above its TTR without an excessive amount of force being applied. For example, the anchoring assembly may be designed such that the bone anchor cavity confines and prevents the coupling member from changing its shape. This in turn would cause strain to develop in the shape memory material and thereby produce the forces which must be overcome in order to extract the coupling member from the bone anchor cavity. It is also envisioned that instead of or in combination with the generation of such strain forces, the shape memory portion of the coupling member may be trained to have a shape which mechanically interlocks with a mating portion of the bone anchor cavity. For example, matching threads may be used which only engage when the anchoring assembly is at its working temperature(s). In this way, the amount of force needed to extract the coupling member out of the cavity of the bone anchor at a given temperature may be controlled by the shape training of the shape memory portion.

The amount of force needed to extract the coupling member from the bone anchor cavity may not only be controlled by the shape memorized but also by the shape memory material selected and its mechanical properties. By selecting a shape memory material having a TTR that falls below the working temperature of the anchoring assembly, the strength and superelastic characteristics of the material, and therefore the strength of the locking force, may be maximized. Lower locking forces may be obtained by choosing a shape memory material having a TTR that overlaps the working temperature(s) of the anchoring assembly. In some applications it may be desirable for the body part to detach from the bone by extraction of the coupling member from the bone anchor rather than risking damage to the body part, such as with soft tissue attachment. The desired locking force may also be obtained by varying the mechanical properties of the shape memory material, such as by material selection or processing. The mechanical properties of many shape memory materials may be varied to a significant degree, particularly shape memory metal alloys.

The coupling member is connectable or attachable to the body part. The coupling member may be attached to the body part directly, such as by a suture threaded through an eyelet formed in the coupling member. It may also be attached to the body part indirectly, such as through a female receptacle, itself attachable to the body part, having an opening leading to a cavity formed therein. With the latter embodiment, the coupling member may have another shape memory portion which has been trained to also be movable in and out of the female receptacle at least at temperatures below a TTR, and while in the female receptacle, trained to be locked thereto when at least at temperatures above its TTR. The present coupling member may be made from different shape memory materials processed such that it is removable from and locked to the bone anchor and female receptacle at different temperatures. The portions of the coupling member which mate with the bone anchor and the female receptacle may also be made from the same shape memory material having the same TTR. In either case, each portion may be separately cooled below and warmed above its TTR in order to selectively release or lock the coupling member from or to either the bone anchor or the female receptacle. In addition, the coupling member and female receptacle may be attached to one another by using the superelastic characteristics of the shape memory material to snap fit, or otherwise, connect the two together. The coupling member and female receptacle may also be connected together using well known techniques and structure such as mating threads, welding or other bonding techniques.

Because the coupling member may be lockable in and removable from the bone anchor implanted in the bone with little, if any, applied force simply by changing the temperature of the applicable shape memory portion, the embedded bone anchor can remain undisturbed if the body part has to be detached from the bone, thus optimizing the strength of the anchorage. In addition, because the coupling member may be inserted and extracted from the implanted bone anchor with little if any insertion and extraction forces being applied (i.e., simply by pushing it in and pulling it out of the bone anchor cavity), the body part may be anchored to locations on the bone having spatial constraints which might limit the applicability of more complex anchoring systems or otherwise require more invasive surgical procedures and cause additional discomfort or trauma for the patient. Furthermore, because it is contained in the bone anchor, the shape memory portion of the coupling member does not directly contact body tissue and is therefore more likely to be compatible with a greater number of patients. Some patients have been known to have undesirable reactions to certain shape memory materials, notably the nickel in nickel-titanium shape memory alloys.

The above and other aspects of the present invention will become apparent upon consideration of the following descriptions taken in conjunction with the accompanying drawings.

BRIEF DESCRIPTION OF THE DRAWINGS

FIG. 1 is a partially sectioned side view of one embodiment of the present anchoring assembly for attaching a dental-prosthesis to a jaw bone in an unlocked condition;

FIG. 2 is a partially sectioned side view of the anchoring assembly of FIG. 1 with its coupling pin locked in place;

FIG. 2A is a side view of how the coupling pin of FIG. 2 would appear if not physically constrained;

FIG. 2B is a side view of how an alternative embodiment of the coupling pin of FIG. 2 would appear if not constrained;

FIG. 2C is a side view of how another alternative embodiment of the coupling pin of FIG. 2 would appear if not constrained;

FIG. 2D is a side view of how a fourth embodiment of the coupling pin of FIG. 2 would appear if not constrained;

FIG. 2E is a side view of a fifth embodiment of the coupling pin of FIG. 2;

FIG. 3 is a partially sectioned side view of a finger joint prosthesis incorporating the principles of the present invention;

FIG. 4 is a partially sectioned and schematic side view of a distraction osteogenesis device incorporating the principles of the present invention;

FIG. 5 is a partially sectioned side view of a modification of the anchoring assembly embodiment of FIG. 4;

FIG. 5A is a partially sectioned side view of an alternative modification of the anchoring assembly embodiment of FIG. 4;

FIG. 6 is a partially sectioned side view of an adjustable bone plate incorporating the principles of the present invention;

FIG. 6A is a partially sectioned enlarged view of the circled area 6A of FIG. 6;

FIG. 7 is a partially sectioned side view of one embodiment of the present anchoring assembly for attaching a body part to bone using a suture;

FIG. 8 is a partially sectioned disassembled side view of the suture anchoring assembly of FIG. 7 and a bone anchor implantation tool;

FIG. 9A is a partially sectioned side view of a modification of the suture anchoring assembly of FIG. 8;

FIG. 9B is a sectional view of FIG. 9A taken along lines 9B—9B;

FIG. 10A is a perspective view of an alternative coupling pin for the suture anchoring assembly of FIG. 8 in either a cooled or constrained condition;

FIG. 10B is a perspective view of the coupling pin of FIG. 10 in a warmed and unconstrained condition;

FIG. 10C is a perspective view of another alternative coupling pin for the suture anchoring assembly of FIG. 8;

DETAILED DESCRIPTION OF THE INVENTION

Figure 11:
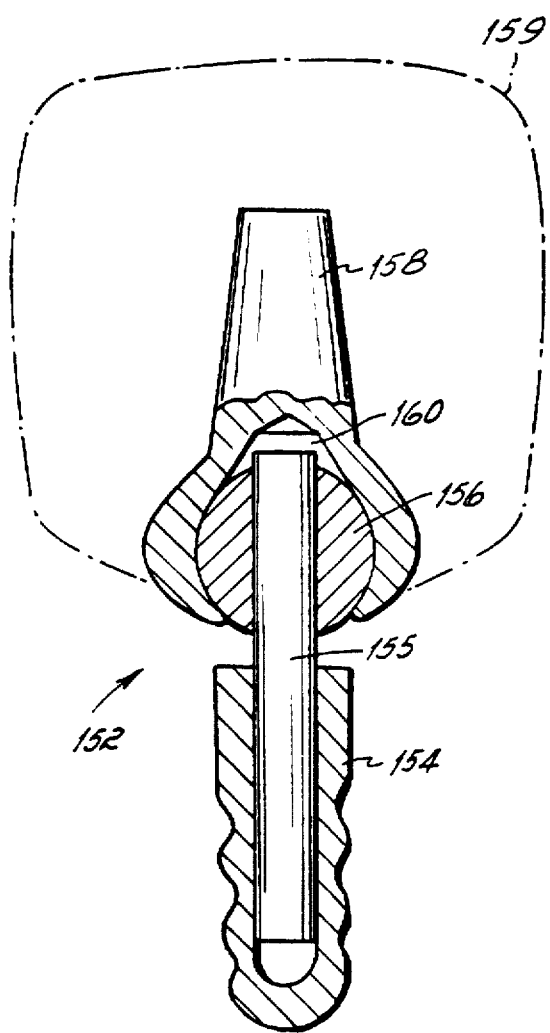
FIG. 11 is a partially sectioned side view of another embodiment of the present anchoring assembly for attaching a prosthesis.

The principles of the present invention shall herein be described in detail with regard to a variety of embodiments and applications of the present bone anchoring assembly.

Referring to FIGS. 1, 2 and 2A, one embodiment of the present anchoring assembly 20 is particularly useful for anchoring a prosthetic device like a tooth 21 (shown in phantom), such as in the form of a crown or bridge, to a patient's jaw bone 22. The anchoring assembly 20 includes a bone anchor 26, such as a root screw, having an opening 27 formed through a top surface 28 and leading to a bore or cavity 29 formed therein. For a patient with the root of the tooth intact and in place (i.e., only the crown fractured off), it may be possible to use the existing root as the bone anchor 26, with its root canal functioning at least as a guide for the cavity 29. The bore 29 has an inside dimension or diameter $D_1$. The root screw 26 is adapted for implantation in the jaw bone 22 such that the top surface 28 is below the patient's gums 32. A temperature sensitive coupling pin 34 is used to fix a female receptacle or stump 35 mounting the prosthetic tooth 21 to the anchor screw 26. At least one portion, and in this embodiment all, of the coupling pin 34 is made of a shape memory material having a transformation temperature range (TTR). The coupling pin 34 has a length L and an outer dimension or diameter $D_2$. The mounting stump 35 has its own opening 37 formed through a lower surface 38 and leading to a cylindrical bore or cavity 39 having an inside dimension or diameter preferably identical to the diameter $D_1$ of the bore 29 in anchoring screw 26.

Briefly, the working temperature or temperature range (e.g., temperatures normally found in the human body) of any shape memory portion of the present invention may be within or above the TTR of the shape memory material(s) being used. The TTR for many shape memory materials, especially shape memory metal alloys, can often be adjusted to compensate for a particular ambient temperature. For some applications, it may be preferable for each shape memory portion of the present invention to have a TTR which falls below the working temperature(s). In other applications, it may be preferable for the TTR to overlap the working temperature(s).

While the present invention is not to be limited to any particular shape memory material, shape memory metals, particularly binary alloys of titanium (Ti) and nickel (Ni) as well as Ni and Ti alloyed with, for example, niobium (Nb), iron (Fe), cobalt (Co), copper (Cn) or manganese (Mn), are of particular interest. With respect to most shape memory metals, two basic crystal structures exist, martensite below the TTR and austenite above the TTR. A combination of both structures, to varying degrees, may exist within the TTR. Generally, martensite is relatively weak and pliable, and austenite is relatively strong with superelastic properties. If the shape memory metal is in the martensitic stage, it will need to be heated to transform to austenite. If the shape memory metal is in the austenitic stage, it will need to be cooled to transform to martensite. When the ambient temperature is within the TTR, the actual structure of the shape memory metal is dependent on its temperature history. When the structure of the shape memory metal is not all but mostly austenite, it can still exhibit superelastic properties. When the structure of the shape memory metal is all or mostly martensite, it may be comparatively weaker and more pliable than the austenite structure, but it can still exhibit some elastic properties (i.e., strained to produce an applied force). Some shape memory metals, commonly known as wide hysteresis alloys can have a wide TTR. With these materials, it is possible to use the martensitic structure during insertion at ambient temperature, thereby enabling adjustment without cooling. Once the adjustment is completed, the memory material is temperature cycled (typically by heating above the TTR) to drop the martensite-to-austenite transformation to a temperature well below ambient temperature. The locking effect would therefore be stable, at a wide range of ambient temperatures. This type of shape memory material is particularly useful when the environment is inside a patient's body where repeated adjustment is often not necessary or desirable but stability is.

For the embodiment of FIGS. 1 and 2, the length L of the coupling pin 34 is sufficient to extend into the cylindrical bore 29 and 39 of the anchoring screw 26 and the mounting stump 35, respectively, at the same time. The shape memory coupling pin 34 is longer and thinner at least when it is at a temperature below the TTR of the shape memory material and, when it has no spatial constraints (see FIG. 2A), it is shorter and thicker at least at temperatures above the TTR of the shape memory material used. This variation in shapes of pin 34 may be accomplished in three basic ways. The coupling pin 34 may be processed to exhibit a 2-way shaped memory, in which case simply cooling or heating pin 34 will cause it to change shape. Pin 34 may also be processed to exhibit only one-way shape memory. This would require the shape memory portion of the coupling pin 34 to be deformed into the desired geometric configuration at a low temperature and then warmed to convert it back to its original geometric configuration (see FIG. 2E and the associated description). As a third method, a wide hysteresis shape memory material may be used which would remain stable even at ambient temperature and would not lock in place until warmed above the ambient temperature.

By making the outer dimension $D_2$ of the coupling pin 34 smaller in size than the inside diameter $D_1$ of the boreholes 29 and 39 at temperatures below its TTR, the pin 34 may be inserted into and extracted from either borehole 29 and 39 with little if any (i.e., substantially zero) insertion and extraction force, respectively, at such temperatures (see FIG. 1). The anchoring pin 34 may also be trained so that its outer dimension $D_2$ is larger than the inside diameter $D_1$ of the bores 29 and 39 at temperatures above the TTR of the shape memory material (see FIG. 2A). In this way, with the anchoring pin 34 being at a temperature above its TTR and disposed in both bores 29 and 39, the pin 34 may be locked to both the anchoring screw 26 and the mounting stump 35, and the prosthetic tooth 21 may be anchored to the patient's jaw bone 22. The force exerted between the coupling pin 34 and the anchoring screw 26 and mounting stump 35 may be varied by changing the outer dimension $D_2$ of the pin 34 reached at the working temperature range in which the anchoring assembly 20 is used. For example, forces as high as 500 newtons have been required to pull a shape memory pin (normally having an unconstrained diameter of 1.43 mm) out of a bore having a diameter of 1.4 mm. With this exemplary system, the shape memory pin was inserted into the bore a depth of about 2 mm. The shape memory material used for the pin was a TiNiNb wide hysteresis alloy. At temperatures below the TTR, the pin had an outside diameter of 1.39 mm.

With the three elements 26, 34 and 35 sharing the same central longitudinal axis 42, it may be difficult to implant the bone anchor 26 such that the prosthetic tooth 21 is properly located relative to the surrounding teeth (not shown). Therefore, it may be desirable to skew the central axis 42 of the stump 35 relative to that of the coupling pin 34 to facilitate positioning of the prosthetic tooth 21 to a desired location relative to the patient's other teeth (not shown).

It may not only be desirable for the expansion of coupling pin 34 in bores 29 and 39 to prevent separation of the stump 35 from the anchoring screw 26, it may also be desirable to prevent rotation of the stump 35 relative to screw 26, up to an ultimate applied force. To aid the locking forces exerted by coupling pin 34 in accomplishing this task, a mechanical locking system may be employed. For example, the pin 34 and either or both bores 29 and 39 may be given matching non-circular cross-sections (e.g., square, oval, etc.). Rotation of the stump 35 may also be prevented by using multiple pins 34 with a corresponding number of matching bores 29 and 39. The respective top and bottom surfaces 28 and 38 of the anchoring screw 26 and mounting stump 35 may also be roughened, such as with mating grooves and ridges (not shown) in order to provide an additional impediment to relative rotation between these two elements 26 and 35 of the anchoring assembly 20. This may also be done with the engaging surfaces between the coupling pin 34 and the bores 29 and 39 to prevent not only such relative rotation but also the stump 35 being pulled away from the anchoring screw 26. For example, see the mating threads shown in FIG. 5. Coupling pin 34 and stump 35 may also be joined by means other than those previously described. For example, instead of using the shape memory properties of the shape memory material, its superelastic characteristics may be utilized. Structures similar to that shown in FIGS. 2B–D (see description below) may be used with the superelastic properties to snap fit or otherwise lock the coupling member 34 and female receptacle 35 together. They may also be threaded together, welded or otherwise bonded together or be of single piece construction.

The principles of the present invention incorporated in the anchoring assembly 20 may also be applied to other prosthetic devices including any body joint, such as a hip joint prosthesis. For example, the bone anchor 26 could be a femoral stem and the female receptacle 35 could be a femoral head adapted for mating with an acetabular cup component of the hip joint prosthesis. Another application may be the anchoring of a prosthetic ear.

Referring to FIGS. 2B–D, alternatively geometric configurations which could be utilized for locking the coupling pin 34 into either or both cavities 29 and 39 may include an aperture 45 formed through the pin 34 which is relatively narrow at temperatures below its TTR, such that the outer dimension $D_2$ of the pin 34 is smaller than the inside diameter $D_1$ of the corresponding cavity 29 or 39. At temperatures above its TTR, the aperture 45 would then be substantially wide enough to cause the outer dimension $D_2$ of coupling pin 34 to be larger than the inside diameter $D_1$ (see FIG. 2B). The coupling pin 34 may also utilize a forked portion 47 having two or more prongs 48 which open up at temperatures above their TTR to a dimension $D_2$ greater than the inside diameter $D_1$ (see FIG. 2C). Coupling pin 34 may also be trained to have a central longitudinal axis 49 that is substantially straight at temperatures below its TTR and substantially curved at temperatures above its TTR to lock the pin 34 in the cavities 29 and 39 (see FIG. 2D). This modified pin 34 may be trained to have two or more bends in its axis 49 along its length L. In general, training a shape memory element to have a two-way shape memory is more difficult than training the material to have a one-way memory. However, the anchoring assembly 20 may be modified to include a tubular biasing sleeve 50 which enables the coupling pin 34 to effectively have a two-way shape memory even if it was trained to only have a one-way memory (see FIG. 2E). The biasing sleeve 50 applies a compressive force against pin 34. Thus, at temperatures below its TTR, the biasing sleeve 50 is intended to reduce the outside diameter of pin 34 enough that it and sleeve 50 may be inserted into the cavity 29 of bone anchor 26. However, when the shape memory material warms to a temperature above its TTR, pin 34 is able to exert enough force to counter these compressive forces and expand biasing sleeve 50 outward, thereby locking itself in bone anchor 26. Preferably, a longitudinal split 51 is formed through the wall of biasing sleeve 50 in order to facilitate this two-way shape memory effect.

Referring to FIG. 3, instead of prosthetic tooth, a prosthetic body joint, such as a finger joint 53, may be attached between two separate bones 54 and 55 using two anchoring assemblies 58 incorporating the 0 principles of the present invention, one for each bone 54 and 55. Each finger joint anchoring assembly 58 includes a bone anchor 59 and a coupling pin 60 having a shape memory portion 61 at one end disposed within the bone anchor 59 in the same manner as previously described for anchoring assembly 20. The coupling pin 60 also includes a portion 62 extending out of bone anchor 59 which is attached to one end of the finger joint 53 by any acceptable means. For example, portion 62 of each coupling pin 60 may have an appropriate shape necessary to adequately maintain each portion 62 disposed inside the finger joint 53. Portion 62 may also be bonded to joint 53. Portion 62 of each anchoring assembly 58 may also be made of a shape memory material, with either or both of its shape memory and superelastic properties being used to attach it to the finger joint 53.

Referring to FIG. 4, instead of two bones being attached to one another through a prosthetic body joint, a distraction osteogenesis device 66 may be anchored between two segments 67 and 68 of bone using two anchoring assemblies 70 incorporating the present invention. Each anchoring assembly 70, similar to the previous anchoring assemblies 20 and 58, includes a bone anchor 73, each embedded in its corresponding bone section 67 and 68, and a coupling pin 75. Each coupling pin 75 has one portion 76 made of a shape memory material having a TTR disposed within the bone anchor 73, similar in manner to that previously described. Each coupling pin 75 also includes another portion 77 extending out of the bone anchor 73 which is adapted for attaching to a bone plate component 80 of the distraction osteogenesis device 66 by any appropriate means. For example, each portion 77 may be in the form of a shank with a head 78. Each coupling pin 75 is disposed through a hole 79 formed in its corresponding bone plate 80. Each bone plate 80 is positioned between its corresponding coupling pin head 78 and bone anchor 73. In this way, each bone plate 80 is secured to its corresponding bone section 67, 68 when the shape memory portion 76 of pin 75 is locked within bone anchor 73. Each of the bone plates 80 may be anchored to its corresponding bone section 67, 68 using any one of the three anchoring assemblies shown in FIGS. 4, 5 and 5A. Each of these anchoring assemblies may also be used to anchor a bone plate component 82 of any device to bone not just that of a distraction osteogenesis device.

Referring to FIG. 5, another anchoring assembly 83 may be used to attach bone plate 80 or any other bone plate component 82 to bone. Anchoring assembly 83 is a modified version of anchoring assembly 70 in which a headed coupling pin 84 is used with a threaded shank 85 and a bone anchor 86 with a threaded bore 87. The threaded portion 85 of pin 84 is made of a shape memory material having a TTR. The threaded portion 85 has been pre-programmed to have an outer dimension or diameter smaller than the inside dimension or diameter of threaded bore 87 when at a temperature below its TTR, thereby enabling the coupling pin 84 to be easily inserted and extracted from bore 87 with substantially zero insertion and extraction forces and without having to screw or unscrew pin 84 from bone anchor 86. The threaded shank 85 is also trained to have an outer diameter larger than the inner diameter of threaded bore 87 when at a temperature above its TTR. The threads on shank 85 and in bore 87 are preferably designed to mate with one another when the threaded shank 85 is in its enlarged condition (i.e., above its TTR). In order to facilitate interlocking between the plate 82 and coupling pin 84, similar matching threads may be employed. In this way, the coupling pin 84 may be made more resistant to being pulled out of bone anchor 86. Optionally, the threaded shank 85 may be modified by being split longitudinally into two or more sections 88 in order to facilitate enlargement of the outer diameter of shank 85, similar to that shown in FIG. 2C. In addition, coupling pin 84 may include a keyed head 89 in case full disengagement between threaded shank 85 and threaded bore 87 does not occur (i.e., the outside diameter of shank 85 remains just slightly larger than the inside diameter of bore 87) at a temperature below the TTR so that the threaded coupling pin 84 may still be inserted and removed. Such a loose fit would still allow insertion and removal with only minimal applied force.

FIG. 5A illustrates an anchoring assembly 92 similar to the anchoring assembly 20 of FIGS. 1 and 2. In addition to the bone anchor or screw 26 and the coupling pin 34, anchoring assembly 92 includes a headed female receptacle or stud 93. As with the anchoring assembly embodiment 20, the portion of coupling pin 34 disposed inside of the female receptacle 93 of assembly 92 may or may not be made of shape memory material. Alternatively, this portion of pin 34 may be secured to the headed stud 93 by some means other than using the shape memory effect. For example, they may be threaded, welded, brazed, or otherwise connected together.

Referring to FIGS. 6 and 6A, a bone plate 94, such as that used for a dental bridge, may be attached to two sections 95 and 96 of bone using two of the present anchoring assembly embodiments 99 in combination with a female receptacle in the form of a lockable ball joint 100. Each anchoring assembly 99, like those previously described, includes a bone anchor 102 and a coupling pin 103. Each ball joint 100 includes an outer casing 105, which could be formed by part of the plate 94, and a split ball 106 having at least one split 107 and a cavity or bore 108 formed therethrough. Bore 108 is adapted to receive a portion 110 of the coupling pin 103. With pin 103 trained in the same manner as pin 34 (see FIGS. 1, 2 and 2A), the thickening of pin 103 at temperatures above its TTR causes the split ball 106 to expand and lock inside of casing 105. In this way, the relative orientation of plate 94 and bone sections 95 and 96 may be stabilized. Split 107 facilitates the expansion of ball 106 in reaction to the thickening of portion 110 of coupling pin 103. It may be desirable to use a split ball 106 with multiple splits 107 to facilitate the transfer of forces from pin 103 even more.

Referring to FIGS. 7 and 8, the present invention is applicable to an anchoring assembly 114 for attaching a body part, such as soft tissue, (not shown) to bone 115 using a suture 118 (shown in phantom). The assembly 114 includes a bone anchor or screw 119 having an opening 120 leading to a stepped bore 123 formed therethrough. The bore 123 has an initial section 124 with a hexagonal shape adapted for receiving an allen wrench 125 with a mating hexagonal cross-section. Bore 123 also includes a deeper section 126 which is cylindrically shaped. A coupling pin 130 is adapted for being inserted into the bore 123 of screw 119. Pin 130 includes a cylindrical shank 131, and a hexagonally shaped head 132 having a cross-section matching that of the allen wrench 125. The coupling pin 130 also includes an eyelet 133 formed above the hexagonal head 132 for threadably receiving the suture 118. At least the shank portion 131 of pin 130 is m ade of a shape memory material having a TTR. Th e shape memory shank 131 and hexagonal head 132 may be fixed together in a number of ways. For example, shank 131 and head 132 may be threadably engaged, welded or otherwise bonded together, or they may be of one piece construction from the same shape memory material. They may also be fixed together using the shape memory effect and structure previously described for the pin 34 and stump 35 (see FIGS. 1 and 2) and the pin 34 and headed stud 94 (see FIG. 5A). The superelastic properties of the shape memory material may also be used to attach shank 131 and head 132 together using well known snap fit or other conventional systems.

Thus, the anchoring assembly 114 may be installed by first drilling a blind bore 137 into the bone 115 and embedding (i.e., screwing) the bone screw 119 into the bore 137 to an appropriate depth using tool 125. Preferably, the bone screw 119 is then left unloaded within bore 137 in order to promote growth and bonding of the bone to the outer surface of screw 119. After a sufficient amount of time has passed, pin 130 is secured to screw 119. With shank 131 having been trained in the same manner as the previously described pin 34, at least the shape memory portion 131 of pin 130 is cooled to a temperature below its TTR such that the outer diameter of shank 131 is smaller than the inside diameter of the bore section 126. Pin 130 is then inserted into stepped bore 123 with shank 131 loosely fitting within bore 126 and head 132 seated in section 124. The loose fit enables the pin 130 to be inserted into bore 123 with substantially zero force. Shank 131 is then allowed to warm up to a temperature above its TTR, thereby causing it to change shape and lock inside of bore section 126 in the same manner as has been described herein for previous embodiments. Optionally, shank 131 may be configured and trained to respond in the same manner as that described for and illustrated in FIGS. 2B–D. With the coupling pin 130 now locked in place within the anchoring screw 119 (see FIG. 7), the body part such as a ligament (not shown) may be anchored to the bone 115 using the suture 118. The mating hexagonal shapes of head 132 and bore section 124 help to prevent the coupling pin 130 from rotating and twisting out of bore 123.

Referring to FIGS. 9A and 9B, instead of the coupling pin 130 with eyelet 133, an alternative coupling pin 140 may be used with bone anchor 119. Pin 140 is basically a headless version of pin 130 with two longitudinal slots or bores 141 and 142 formed along its length. Each slot 141 and 142 is dimensioned to allow the passage of the suture 118 therethrough. Pin 140 is made of a shape memory material having a TTR and has been similarly dimensioned and trained as the shank 131 of the previous coupling pin 130. Therefore, pin 140 may be locked within screw 119 and a body part (not shown) anchored in place with the suture 118 using the same cooling and warming technique previously described.

Referring to FIGS. 10A–C, a number of other coupling pin designs may be suitable for use with a bone anchor, like screw 119. One such coupling pin 144 has a tubular section 145 with a longitudinal split 146 along its length formed through to its central bore 147. The shape memory pin 144 is trained so that its split 146 is closed enough at temperatures below its TTR to permit the section 145 to be inserted through bore section 123. Pin 144 is further programmed such that its split 146 opens, as shown in FIG. 10B, when it is allowed to warm unconstrained to a temperature above its TTR outside bore section 123. Central bore 147 is dimensioned to permit the suture 118 to be threaded therethrough. As previously described for other embodiments, the outer diameter of the tubular section 145 of pin 144 is smaller than the inside diameter of bore section 126 at temperatures below the TTR and larger than the inside diameter of bore section 126 at temperatures above the TTR. Pin 144 may then be locked within screw 119 by cooling and then warming pin 144 in the same manner as described for the previous coupling pin embodiments 130 and 140. With having been previously threaded through central bore 147, suture 118 may be secured to pin 144 by tying a knot 148 at its end before pin 144 is inserted into the screw 119. In order to increase the versatility of the suture anchoring assembly 114, pin 144 may include a head 149 with the split 146 and bore 147 also being formed therethrough. With the head 149, the suture anchoring assembly 114 could serve another purpose, such as the same applications shown in FIGS. 4, 5 and 5A. Optionally, pin 144 may be designed without split 146 (see FIG. 10C). In which case, tubular section 145 would simply become thinner and thicker in the same manner as previously described for pin 34 (see discussion for FIGS. 1, 2 and 2A–E). In addition, instead of using a tubular construction for the coupling member of suture anchoring assembly 114, other shapes may be desirable. For example, a shape memory sphere or ball may be used instead of pin 140 or 144. Such a ball may have one or more bores through which the suture 118 may be threaded in the same manner as shown in FIGS. 9A and 9B and 10A–C. A shape memory ring may also be used instead of pin 140 or 144. Such a ring may have an oval or otherwise flattened shape at lower temperatures so that it may be inserted into bore section 126 and a circular shape, if unconstrained by bore section 126.

Figure 11A:
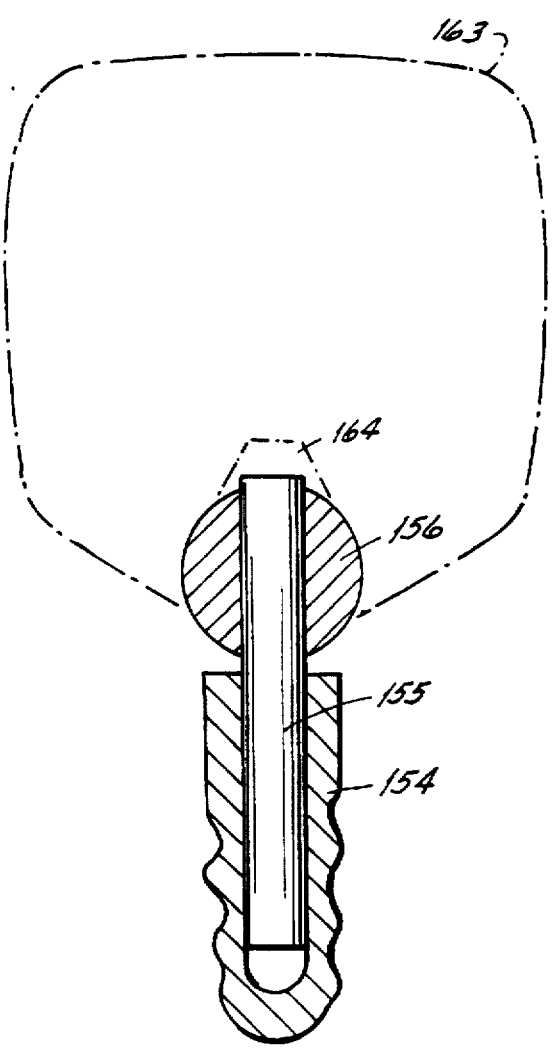
FIG. 11A is a partially sectioned side view of a modification of the anchoring assembly of FIG. 11.

Referring to FIGS. 11 and 11A, the principles of the anchoring assembly 20 (see FIGS. 1 and 2) may be combined with those of the lockable ball joint 100 (see FIGS. 6 and 6A) in order to produce another anchoring assembly embodiment 152 of the present invention. Assembly 152 includes a bone anchor or screw 154 and a shape memory coupling member or pin 155 adapted to be received within bone screw 154 in the same manner as that previously described for screw 26 and pin 34 of assembly 20. Assembly 152 also includes a split ball 156 and a stump 158. Split ball 156 is structurally similar to split ball 106. Split ball 156 is adapted to receive pin 155 in the same manner that ball 106 receives pin 103 in anchoring assembly 99. Stump 158 is adapted for mounting a prosthetic body part such as a tooth 159. Stump 158 functions like outer casing 105 in that stump 158 has a cavity 160 adapted to receive split ball 156. Thus, stump 158 is slidable around ball 156 and may be tilted relative to pin 55 and screw 54 at least at temperatures below the TTR of the shape memory pin 155. The position of stump 158 relative to pin 155 in screw 154 is fixed at least at temperatures above the TTR of shape memory pin 155. Thus, prosthetic body part 159 may be tilted at any desirable angle relative to coupling member 155 and bone anchor 154 and fixed at that angle in the same manner as previously described for plate 94 and anchoring assembly 99. Alternatively, instead of using stump 158, a prosthetic body part 163 could be provided with a cavity 164 adapted to receive split ball 156 in the same manner as cavity 160 (see FIG. 11A). In either case, the position of the body part 159 and 163 relative to their respective bone anchors 154 may be adjusted or fixed by respectively cooling or warming the corresponding coupling member 155 according to the principles of the present invention, as previously taught herein.

From the above disclosures of the general principles and detailed description of exemplary embodiments incorporating principles of the present invention, those skilled in the art will readily appreciate the various changes and modifications to which the present invention is susceptible. Therefore, the scope of the present invention should be limited only by the following claims and equivalents thereof.

What is claimed is:

1. An anchoring assembly for attaching a body part to bone comprising:

a bone anchor having a first opening leading to a first cavity formed therein and being implantable in the bone; and a coupling member having one portion made of a first shape memory material with a first transformation temperature range and being movable through the first opening and in and out of the first cavity of said bone anchor when at a temperature below the first transformation temperature range, and while in the first cavity, the one portion of said coupling member being locked to said bone anchor when at a temperature above the first transformation temperature range, said coupling member being attachable to the body part, and said one portion of said coupling member having a length and a thickness and, relative to itself, being longer and thinner when at a temperature below the first transformation temperature range and being shorter and thicker when at a temperature above the first transformation temperature range.

2. The anchoring assembly of claim 1, said coupling member being insertable into and extractable from the first cavity of said bone anchor with substantially zero insertion and extraction forces, respectively, when the one portion of said coupling member is at a temperature below the first transformation temperature range.

3. The anchoring assembly of claim 1, the one portion of said coupling member having a longitudinal axis, the longitudinal axis being substantially straight when the one portion of said coupling member is at a temperature below the first transformation temperature range and, while outside of the first cavity, being substantially curved when at a temperature above the first transformation temperature range.

4. The anchoring assembly of claim 1 including a connector interconnecting said coupling member and the body part.

5. The anchoring assembly of claim 4, said connector including a female receptacle having a second opening leading to a second cavity formed therein and another portion of said coupling member being securable inside the second cavity of said female receptacle.

6. The anchoring assembly of claim 5, said female receptacle including a stump fixable to a prosthetic body part.

7. The anchoring assembly of claim 5, said female receptacle including a prosthetic body part.

8. The anchoring of assembly of claim 5, said female receptacle including a portion of a prosthetic body part from the group of prosthetic body parts consisting of a prosthetic tooth, ear, finger joint, hip joint, and any other body joint.

9. The anchoring assembly of claim 5, said female receptacle including part of a bone plate.

10. The anchoring assembly of claim 9, said female receptacle including part of a distraction osteogenesis device.

11. The anchoring assembly of claim 5, said female receptacle being a headed stud.

12. The anchoring assembly of claim 1, said coupling member being a headed shank.

13. The anchoring assembly of claim 1, the first cavity of said first bone anchor having an inside diameter and being threaded, the one portion of said coupling member being a threaded shank having an outer diameter, the outer diameter of said shank being smaller than the inner diameter of the first cavity when said shank is at a temperature below the first transformation temperature range and the outer diameter of said shank being larger than the inner diameter of the first cavity when said shank is at a temperature above the first transformation temperature range.

14. The anchoring assembly of claim 1, said bone anchor being a bone screw.

15. The anchoring assembly of claim 1, the one portion of said coupling member being a tube.

\* \* \* \* \*